US00PP29089P2

(12) United States Plant Patent
Zeppa

(10) Patent No.: US PP29,089 P2
(45) Date of Patent: Mar. 13, 2018

(54) APPLE TREE NAMED 'RS103-110'

(50) Latin Name: *Malus domestica*
Varietal Denomination: RS103-110

(71) Applicant: State of Queensland Through the Department of Agriculture and Fisheries, Brisbane (AU)

(72) Inventor: Aldo Zeppa, Brisbane (AU)

(73) Assignee: STATE OF QUEENSLAND THROUGH THE DEPARTMENT OF AGRICULTURE AND FISHERIES, Brisbane (AU)

( * ) Notice: Subject to any disclaimer, the term of this patent is extended or adjusted under 35 U.S.C. 154(b) by 0 days.

(21) Appl. No.: 15/330,343

(22) Filed: Sep. 8, 2016

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

(56) References Cited

PUBLICATIONS http://www.organicagcenter.ca/AppleSymposium/Organic%20Apple%20and%20Pear%20Conference/Middleton.pdf; 2006; 44 pages.*

* cited by examiner

*Primary Examiner* — Kent L Bell
(74) *Attorney, Agent, or Firm* — Morrison & Foerster LLP

(57) ABSTRACT

A new and distinctive variety of a *Malus domestica* apple tree, named 'RS103-110' that is distinguished by its medium vigor tree, fruit that matures immediately after 'Royal Gala', fruit that is small to medium in size with an obloid to globose shape and a foreground stripe that is dark red in color over a background that is yellow-green in color, fruit stem (pedicel) that can be very short and thick at the point of attachment to the spur, and resistance to apple scab, is disclosed.

6 Drawing Sheets

Latin name:
Botanical classification: *Malus domestica.*
Varietal denomination: The varietal denomination of the claimed apple tree variety is 'RS103-110'.

BACKGROUND OF THE INVENTION

Apples are an economically important crop. Accordingly, there exists a need to develop new varieties of apple tree with improved characteristics, such as disease resistance.

BRIEF SUMMARY OF THE INVENTION

In order to meet these needs, the present invention is directed to an improved variety of apple tree. In particular, the invention relates to a new and distinct variety of apple tree (*Malus domestica*), which has been denominated as 'RS103-110'.

'RS103-110' was identified in Applethorpe, Queensland Australia, and originated from a cross between seed parent 'Royal Gala' (U.S. Plant Pat. No. 4,121) and the proprietary pollen parent 'CPR7T90'. The new variety was selected for its unique traits (e.g., disease resistance) and evaluated at a research facility located in Applethorpe, Queensland Australia.

The new variety of apple tree was first asexually propagated in Year 1 by taking scion wood from the original seedling of 'RS103-110' and top worked onto mature 'Royal Gala' apple trees on 'MM.106' rootstock. Scion wood was subsequently taken from these top worked trees to graft onto a range of rootstocks for a large scale productivity research trial which was planted at the research facility in Applethorpe, Queensland Australia in Year 3. 'RS103-110' has been found to reproduce true to type through the two generations of successive asexual propagations via scion wood grafting and budding onto rootstock.

The original 'RS103-110' apple tree and progeny have been observed growing in a cultivated area of Applethorpe, Queensland Australia. The new variety of apple tree produces fruit that matures for commercial harvesting in approximately mid-February to early-March in Queensland, Australia. This is later than the fruit of 'Royal Gala', which matures for commercial harvesting in early February to mid-February.

The 'RS103-110' apple tree variety is distinguished from 'Royal Gala' by the following unique combination of characteristics:

a. Grows into a medium vigor tree with fruit that matures immediately after 'Royal Gala' and strains of 'Royal Gala';
b. Fruit is small to medium in size with an obloid to globose shape;
c. Fruit has a foreground stripe that is dark red in color over a background that is yellow-green in color;
d. Fruit stem (pedicel) can be very short and thick at the point of attachment to the spur; and
e. Tree and fruit are resistant to apple scab (black spot) caused by races 1 to 5 of the fungus *Venturia inaequalis.*

The 'RS103-110' apple tree variety is distinguished from 'CPR7T90' by the following unique combination of characteristics:

a. 'RS103-110' matures approximately six to seven weeks earlier than 'CPR7T90', which matures mid-season; and
b. Fruit of 'RS103-110' has a foreground stripe that is dark red in color over a background that is yellow-green in color, whereas fruit of 'CPR7T90' is a solid red (RHS 46A) block color, without apparent stripes.

The 'RS103-110' apple tree variety may be further distinguished from presently available apple tree varieties, for example, from 'Red Delicious' and 'Fuji', by the following distinguishing characteristics:

a. Tree and fruit are more disease resistant than are the tree and fruit of 'Red Delicious' and 'Fuji'. Tree and fruit are resistant to apple scab (black spot) caused by races 1 to 5 of the fungus *Venturia inaequalis*, whereas tree and fruit of 'Red Delicious' and 'Fuji' are susceptible to apple scab (black spot) caused by races 1 to 5 of the fungus *Venturia inaequalis*.

Asexual reproduction of the 'RS103-110' apple tree variety by grafting and budding onto rootstock shows that the foregoing and all other characteristics and distinctions are true to type and are established and transmitted through succeeding asexual propagations.

BRIEF DESCRIPTION OF THE DRAWINGS

The 'RS103-110' apple tree variety is illustrated by the accompanying photographs which show fruit of the tree, as well as the flowers. The colors shown are as true as can be reasonably obtained by conventional photographic procedures. However, the colors in the photographs may vary with lighting conditions and, therefore, color characteristics of this new variety should be determined with reference to the observations described herein, rather than from the photographs alone. The photographs are from trees that are 10 years old.

DETAILED BOTANICAL DESCRIPTION

Figure 1:
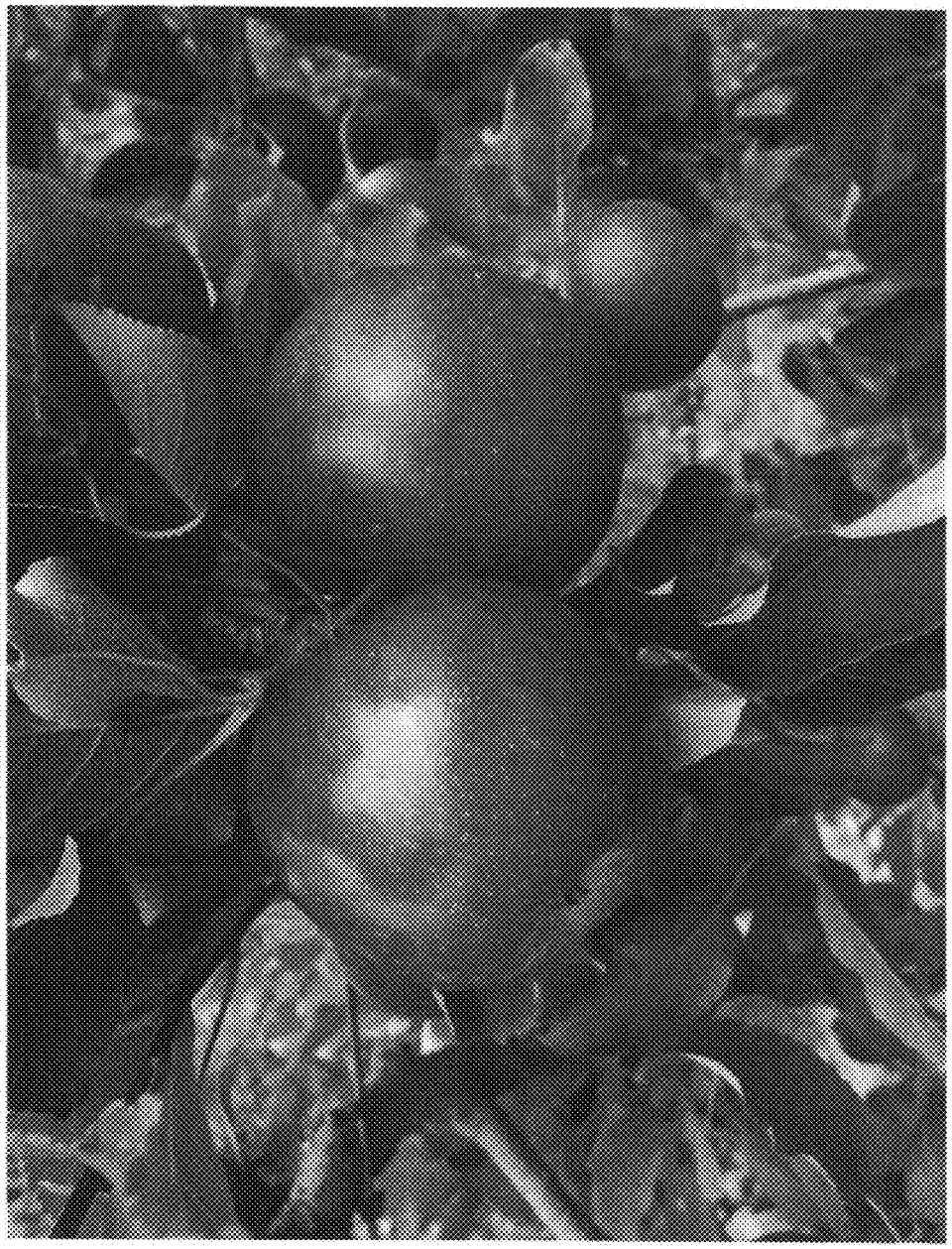
FIG. 1 illustrates fruit of apple tree variety 'RS103-110'.
Figure 2:
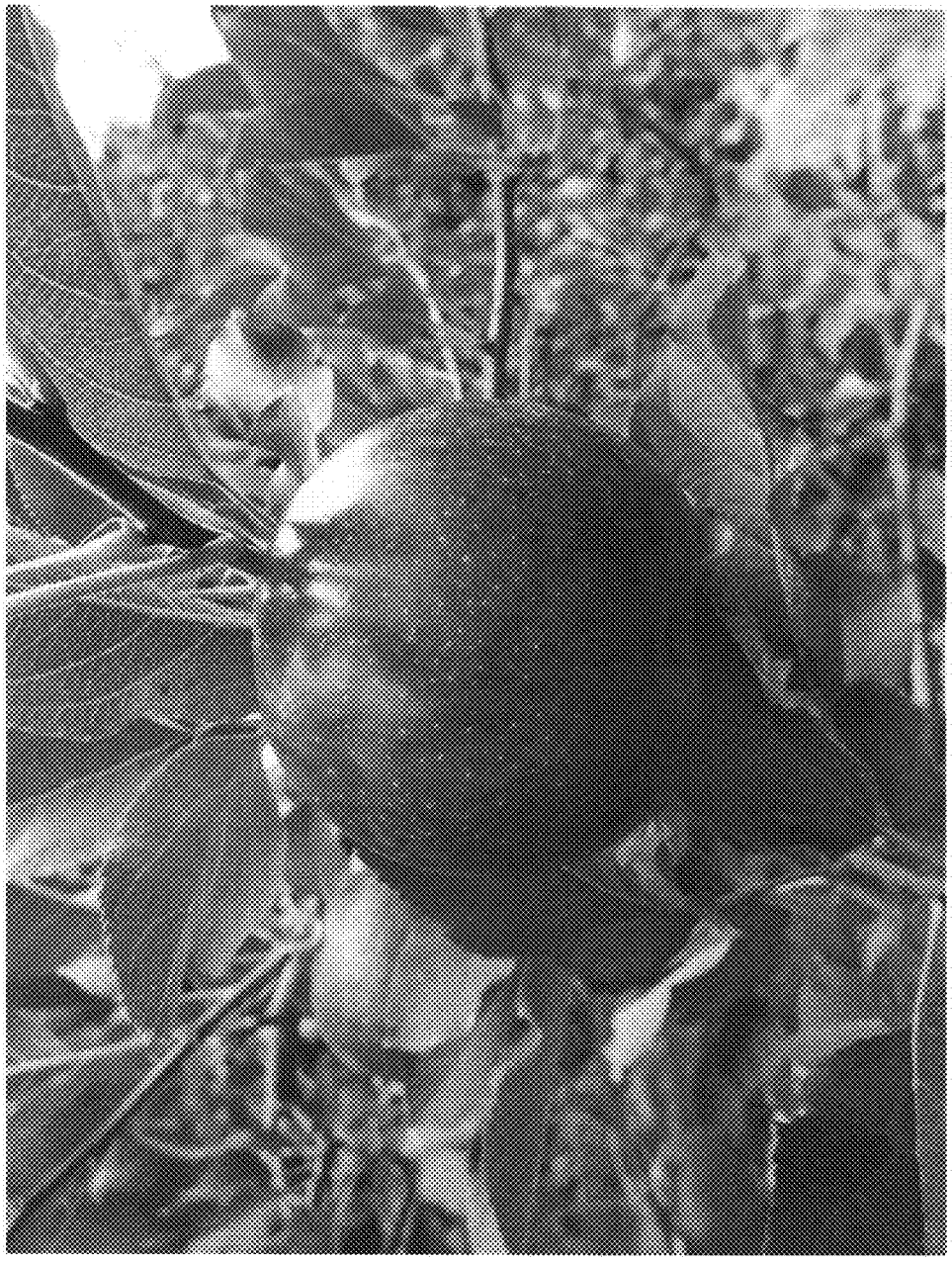
FIG. 2 illustrates the colored side of fruit of apple tree variety 'RS103-110'.
Figure 3:
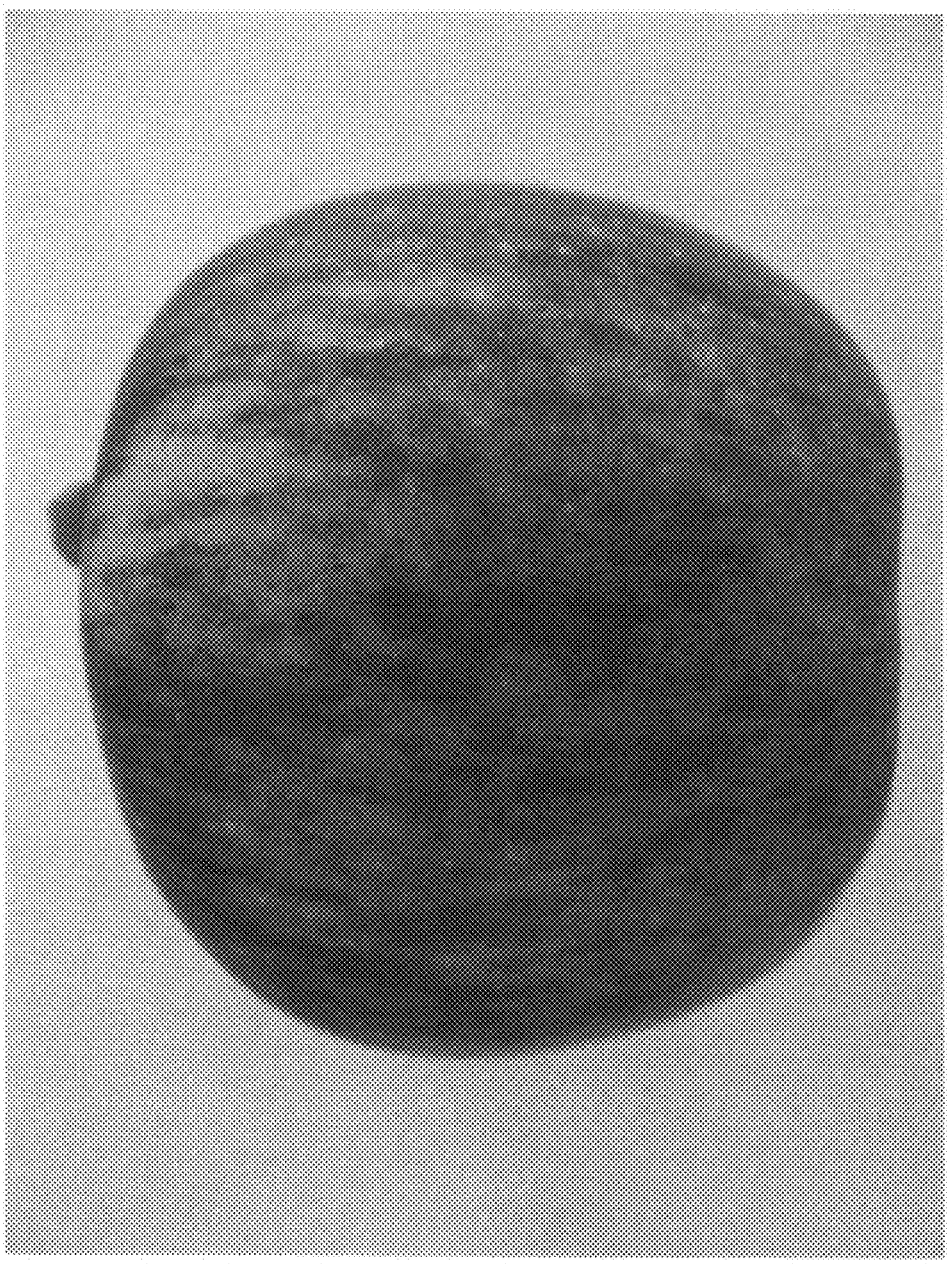
FIG. 3 illustrates the reverse side of fruit of apple tree variety 'RS103-110'.
Figure 4:
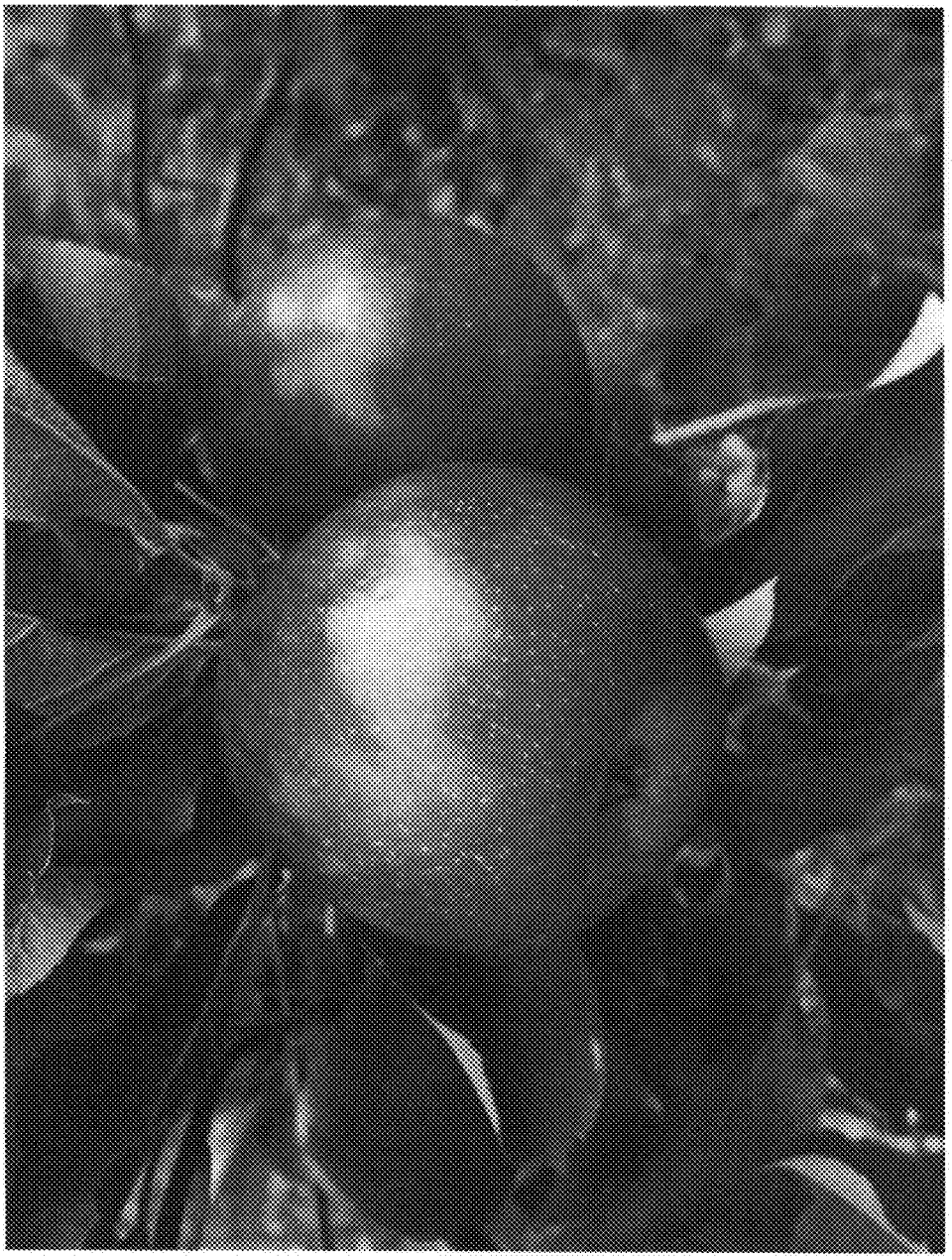
FIG. 4 illustrates fruit of apple tree variety 'RS103-110' on the tree (colored side).
Figure 5:
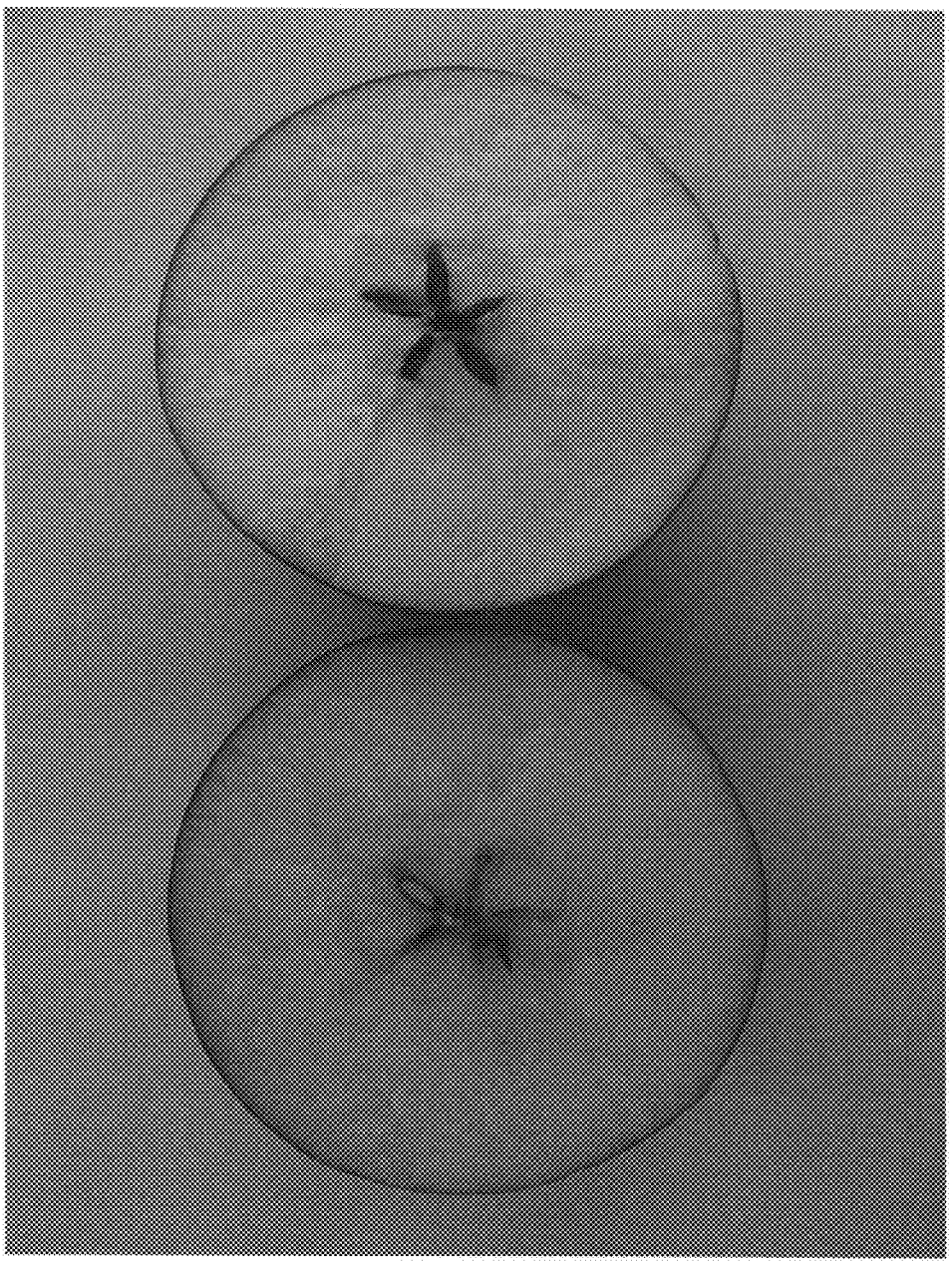
FIG. 5 illustrates the inside flesh of fruit of apple tree variety 'RS103-110'.
Figure 6:
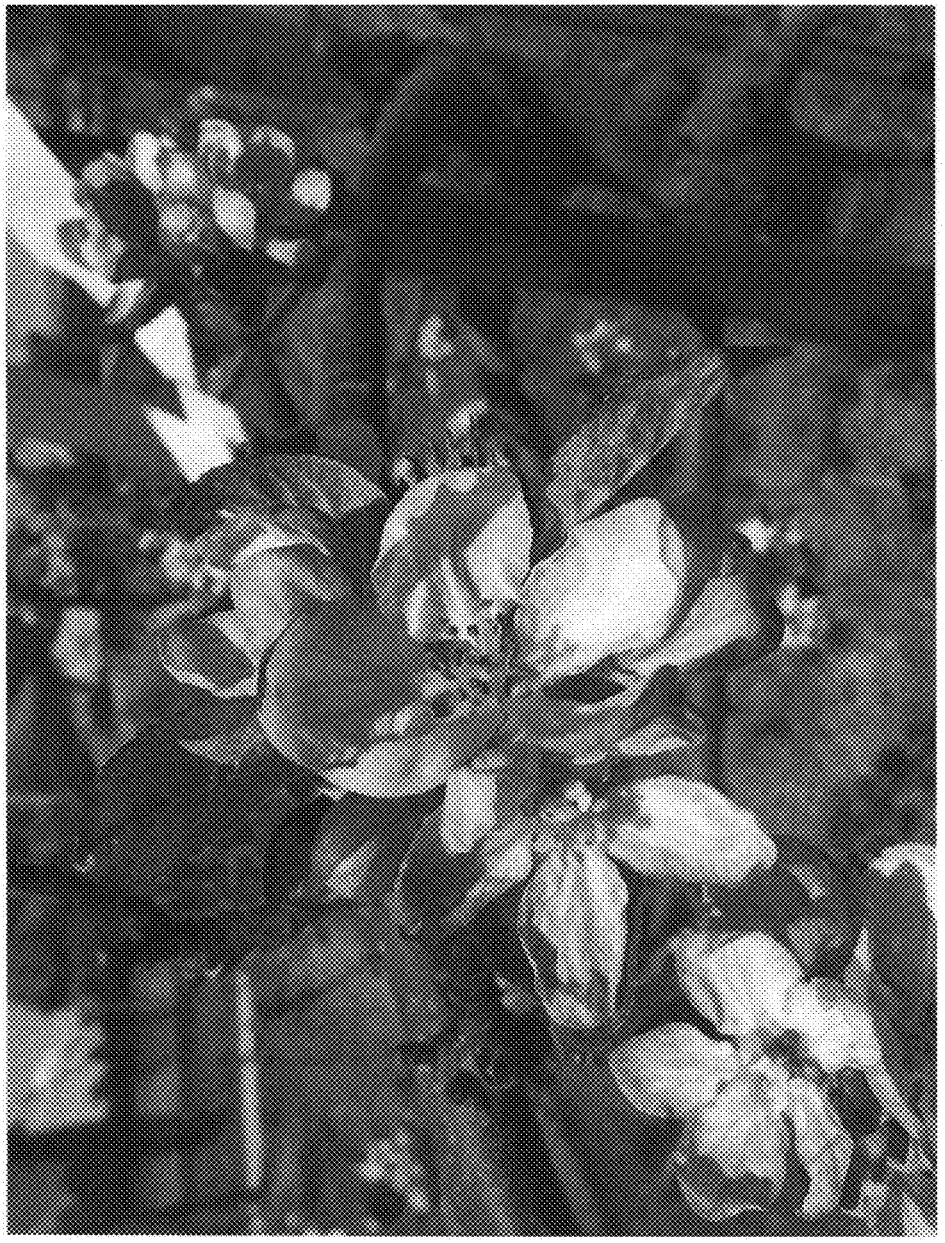
FIG. 6 illustrates flowers of apple tree variety 'RS103-110'.

The following description sets forth the distinctive characteristics of 'RS103-110'. The following description is based on the originally identified apple tree and asexually reproduced progeny, grown on 'M.26' rootstock at the research facility in Applethorpe, Queensland Australia.

Unless otherwise stated, the following description is based on observations from 10-year-old trees growing on 'M.26' rootstock in Queensland, Australia.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. All color references are from *The R.H.S. Colour Chart* by The Royal Horticultural Society.

Tree:

*Vigor*.—Low to moderate.

*Overall shape*.—Spreading to slight drooping.

*Height*.—Approximately 2.02 m.

*Width*.—Approximately 1.60 m.

*Caliper*.—Approximately 57 mm at 100 mm above the graft union, and ranging from approximately 210 mm to approximately 320 mm above the ground.

*Trunk*.—Medium Stocky.

*Trunk bark texture*.—Smooth with raised, prominent lenticels.

*Trunk lenticels*.—Density, approximately 5/cm$^2$; Shape: Round; Color: About Yellow-White RHS 158A. Size: ranging from approximately 0.2 mm to 0.4 mm in diameter.

*Trunk bark color*.—About Grey RHS 201C.

*Patches or other markings*.—No prominent spots or scales evident.

*Primary branches*.—Stout; branches emerge at an angle of approximately 60 to approximately 90 degrees with branches higher in the tree emerging at approximately 60 degrees. Exemplary 2-year-old primary branches have been observed to have a caliper of approximately 11.4 mm measured at the base. Measured trees are grown to a central leader system. The typical and observed lateral branch length is 117.1 cm (first primary branch above graft union and arising from main stem). The diameter of the stem/trunk of the tree measured by caliper at 300 mm above the crotch was an average of 43.0 mm (the crotch on a central leader tree being identified as the point where the first lateral limb emerges).

*Branch color*.—One-year old branches are about Brown RHS 200B in color, while older branches are about Black RHS 202C in color.

*Branch pubescence*.—Absent.

*Branch lenticels*.—Low to medium density, approximately 7/cm$^2$; Shape: Round to Oval; Color: About Yellow-White RHS 158A. Size: ranging from approximately 0.4 mm in diameter to 1.5 mm long by approximately 0.9 mm wide.

*Internodes*.—Average internode length is approximately 2.2 cm for a 1-year old shoot.

*Bearing*.—Annual.

*Hardiness*.—Australian Zone hardy, comparable to 'Cripps Pink'.

*Drought and insect resistance*.—Comparable to 'Cripps Pink'.

*Disease resistance*.—Bred using parent with Vf gene complex conferring resistance to apple scab incited by the fungus *Venturia inaequalis*.

Leaves:

*Texture*.—Leathery.

*Sheen*.—Medium Glossy to slightly dull.

*Length*.—Approximately 6.3 cm to approximately 11.4 cm; average approximately 8.8 cm (average measurement from 50 typical leaves).

*Width*.—Approximately 3.5 cm to approximately 7.0 cm, average approximately 4.9 cm (average measurement from 50 typical leaves).

*Petiole*.—Length: Approximately 35.5 mm. Diameter: Approximately 1.6 mm. Color: About Yellow-Green RHS 144A, tinged with about Greyed-Purple RHS 185B at point of attachment.

*Margin*.—Finely serrated.

*Tip surface*.—Acute.

*Stipules*.—Either 1 or 2 present on 72% of leaves. Where present, opposite, slender (approximately 0.14 mm to approximately 0.95 mm), color about Yellow-Green RHS 144A, length approximately 3.3 mm to approximately 15.7 mm.

*Leaf color*.—Upper leaf surface: About Green RHS 137A. Lower leaf surface: About Yellow-Green RHS 146C.

*Leaf vein color*.—From about Greyed-Purple RHS 185B at the base of the leaf (point of attachment to petiole) to about Yellow-White RHS 145C at the apex.

*Pubescence*.—Absent to very fine on upper surface, to fine (light) on lower surface but thicker on the veins.

Flower:

General:

*Size*.—Medium. Approximately 40.3 mm in diameter fully flattened.

*Shape*.—Ovoid to round.

Unopened bud:

*King bloom length*.—Approximately 10.4 mm to approximately 12.7 mm (average approximately 11.7 mm).

*Diameter*.—Approximately 8.8 mm to approximately 9.8 mm (average approximately 9.4 mm).

*Color*.—About Red-Purple RHS 60C.

Opened bud:

*Color*.—About White RHS 155C with streaks to about Red-Purple RHS 69B to Purple RHS 75C. Flower: Upper petal surface: About White RHS 155C to about Red-Purple RHS 69B. Lower petal surface: About White RHS 155D to about Red-Purple RHS 69B.

Petals:

*Numbers of petals per flower*.—5.

*Petal size*.—Length: Approximately 17.2 mm. Width: Approximately 14.7 mm.

*Petal shape*.—Ovate in shape. Base: Slightly acuminate. Apex: Rounded.

*Arrangement*.—Separated but overlapping.

Sepals:

*Number*.—About 5 per flower.

*Length*.—Approximately 6.61 mm.

*Width*.—Approximately 2.20 mm.

*Color*.—Both upper and lower sepal surface: About Yellow-Green RHS 144A.

*Arrangement*.—Arranged separately.

Pedicel/peduncle: Apples do not have branched inflorescences hence no pedicels. The flower stalk of an apple is the peduncle.

*Length*.—Approximately 17.21 mm (measured to where receptacle is swelling).

*Diameter*.—Approximately 1.23 mm.

*Color*.—About Yellow-Green RHS 144B ranging to Greyed-Green RHS 195A.

Stamen:

*Number*.—Approximately 18 to 20 per flower, arranged in a row around the circumference of the receptacle.

*Length*.—Approximately 9.29 to approximately 11.08 mm.

*Filament color*.—About Greyed-White RHS 156C.

*Anthers*.—About 18 to 20 per flower. Anther Color: About RHS 5A Unopened Anther Color: About Yellow RHS 5A.

*Pollen color*.—About Yellow RHS 4B.

Pistil:

*General*.—The stigma is about approximately 0.5 mm long; styles are 5 in number, separated at base but held tightly and entangled by fine hairs, and about Yellow-Green RHS 144B in color.

Pollination requirements: An early flowering variety e.g., 'Braeburn' or 'Sundowner' is preferred. Later flowering varieties e.g., 'Granny Smith' or 'Cripps Pink' will overlap sufficiently in flowering to enable pollination.

Fragrance: Slight.

Bloom season: In Year 14 at the research station in Queensland Australia, blooming began on the 17$^{th}$ of September with full bloom on the 28$^{th}$ of September finishing on the 5$^{th}$ of October.

Fruit:

General: Measurements are the average of 10 typical 'RS103-110' apples. Size: Small to medium.

*Length*.—Approximately 62.4 mm.

*Width*.—Approximately 72.7 mm.

Shape: Obloid to globose; no lobes observed at calyx end. The calyx ranges from slightly open to open (0.6 mm to 6.1 mm, with an average of 2.4 mm for 10 fruit).

*Cavity*.—Approximately 29.9 mm wide with a depth of approximately 13.1 mm.

*Basin*.—Concave shaped and approximately 28.4 mm wide with a depth of approximately 6.9 mm.

Fruit stem:

*Length*.—Approximately 14.6 mm.

*Diameter*.—Approximately 2.2 mm.

*Color*.—About Yellow-Green RHS 152A to 152D.

Locules: 5 moderately open locules with seeds free of the carpel wall at maturity. Locule length approximately 15.2 mm (average of 50 locules from 10 fruit cut longitudinally). Locule width approximately 7.9 mm (average of 50 locules from 10 fruit with transverse cut).

Fruit skin:

*Tendency to crack*.—Absent

*Thickness*.—Thin.

*Surface texture*.—Glossy with a tendency to become greasy at maturity.

*Lenticels*.—Are present, approximately 0.2 to approximately 0.4 mm in diameter, generally cream in color (yellow-white RHS 158A), and at an average density of about 5 lenticels/cm$^2$.

*Color*.—General color effect: About Red RHS 53A. Ground color: At maturity, about Yellow RHS 2C. Over color: About Red RHS 53A with paler sections about Red RHS 46B. Russetting: Slight amount inside stem cavity.

Flesh:

*Flavor*.—Mild, sweet, low-acid flavor.

*Brix*.—Approximately 10.9 to approximately 13.5 Brix (Average approximately 12.9 Brix).

*Juiciness*.—Moderately juicy.

*Color*.—About Yellow-White RHS 158A.

*Aroma*.—Slight.

Core: While the calyx can be open in about 60 percent of fruit, the calyx tube is closed and the core lines are defined.

*Shape*.—Round to slightly elongate.

*Diameter*.—Approximately 24.7 mm.

*Number of bundles*.—Approximately 10 per fruit.

*Core length*.—Approximately 41.1 mm (measured from point of fruit stem attachment to calyx end at point of sepal attachment).

*Calyx tube length*.—Approximately 13.7 mm (measured as length from the calyx end at point of sepal attachment to the point of calyx tube closure).

Seed:

*Number*.—About 1 to 2 seeds per cell.

*Shape*.—Acute in shape.

*Length*.—Approximately 9.56 mm.

*Width*.—Approximately 5.0 mm.

*Color*.—About Greyed-Orange RHS 175A.

Fruit production: First picking date in the Year 13 season at the research station in Queensland Australia was about the $9^{th}$ of February, and last picking date was about $26^{th}$ of February.

Storage: Fruit remains fresh at room temperature (approximately 20° C.) for approximately 7 days, and can be stored up to approximately 4 months in cold storage (about 1° C. or about 34° F.).

Usage: Fresh eating.

COMPARISONS TO COMMERCIAL APPLE TREE VARIETIES

Ten typical apples of 'RS103-110' and of the cultivar 'Royal Gala' from trees growing near to one another, were obtained on the $18^{th}$ of February and $5^{th}$ of February of Year 13, respectively, and tested for the traits listed in Table 1. The approximate average values of the traits for 'RS103-110' and 'Royal Gala' are listed in Table 1.

TABLE 1

| Trait | 'RS103-110' | 'Royal Gala' |
|---|---|---|
| Firmness (pressure kg/cm$^2$) | 9.0 | 7.4 |
| Starch Index on scale of 1 (high starch) to 6 (low starch) | 5.5 | 5.7 |
| Soluble Solids | 12.9% | 13.6% |
| Apple scab resistance | Resistant | Susceptible |

What is claimed is:

1. A new and distinct variety of apple tree designated 'RS103-110' as illustrated and described herein.

* * * * *